(12) United States Patent
Dwyer et al.

(10) Patent No.: US 8,598,387 B2
(45) Date of Patent: Dec. 3, 2013

(54) PROCESS FOR THE PREPARATION OF ATOVAQUONE

(75) Inventors: Andrew Neil Dwyer, Singapore (SG); Andrew Gordon, Montrose (GB); Michael Urquhart, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/993,683

(22) PCT Filed: Dec. 13, 2011

(86) PCT No.: PCT/EP2011/072600
§ 371 (c)(1),
(2), (4) Date: Jun. 13, 2013

(87) PCT Pub. No.: WO2012/080243
PCT Pub. Date: Jun. 21, 2012

(65) Prior Publication Data
US 2013/0267717 A1      Oct. 10, 2013

Related U.S. Application Data

(60) Provisional application No. 61/423,142, filed on Dec. 15, 2010.

(51) Int. Cl.
*C07C 49/603*   (2006.01)
*C07C 69/78*    (2006.01)
*C07C 45/42*    (2006.01)
*C07D 307/88*   (2006.01)
*C07D 311/76*   (2006.01)

(52) U.S. Cl.
USPC ........... 568/328; 568/316; 549/285; 549/319; 560/51

(58) Field of Classification Search
USPC .............. 549/285, 310; 568/316, 328; 560/51
See application file for complete search history.

(56) References Cited

U.S. PATENT DOCUMENTS 5,856,362 A      1/1999   Hudson

FOREIGN PATENT DOCUMENTS

WO    2008/122988    10/2008
WO    2010/001379    1/2010

OTHER PUBLICATIONS

Barcia, et al., Palladium-catalyzed synthesis of o-acetylbenzoic acids: a new, efficient general route to 2-hydroxy-3-phenyl-1,4-naphthoquinones and indolo[2,3-b]naphthalene-6,11-diones: Tetrahedron Letters 43(29): 5141-5144 (2002).

*Primary Examiner* — Bernard Dentz
(74) *Attorney, Agent, or Firm* — Bonnie L. Deppenbrock

(57) ABSTRACT

Disclosed herein is novel process for preparation of atovaquone, which process includes reacting 1H-2-benzopyran-1,4(3H)-dione with 4-(4-chlorophenyl)cyclohexanecarbaldehyde. The invention further discloses novel intermediates useful in the preparation of atovaquone.

14 Claims, No Drawings

PROCESS FOR THE PREPARATION OF ATOVAQUONE

This application is filed pursuant to 35 U.S.C. §371 as a United States National Phase Application of International Patent Application Serial No. PCT/EP2011/072600 filed Dec. 13, 2011, which claims priority to U.S. Provisional Application No. 61/423,142 filed Dec. 15, 2010, and the entire contents of each of the foregoing applications are hereby incorporated by reference.

FIELD OF THE INVENTION

The present invention relates to a new process for the preparation of atovaquone. In particular, the present invention relates to novel intermediates useful in the preparation of atovaquone.

BACKGROUND OF THE INVENTION

Atovaquone, 2-[trans-4-(4-chlorophenyl)cyclohexyl]-3-hydroxy-1,4-naphthoquinone (compound of formula (I))

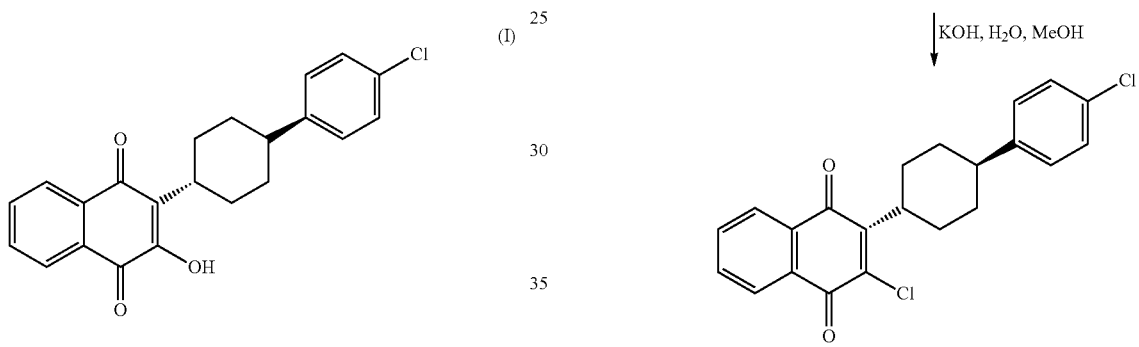

is a useful medicine for the treatment and prophylaxis of *Pneumocystis carinii* infections. Atovaquone is potently active (in animals and in vitro) against *Pneumocystis carinii*, *Plasmodia*, and tachyzoite and cyst forms of *Toxoplasma gondii*. Due to its inhibitory effect in sensitive parasites, atovaquone can act by selectively affecting mitochondrial electron transport and parallel processes such as ATP and pyrimidine biosynthesis.

Atovaquone is approved for marketing in the US under the tradename Mepron® as tablets of 250 mg and an oral suspension which is indicated for the treatment and prophylaxis of *Pneumocystis carinii* infection. It is also available in combination with proguanil hydrochloride under the tradename Malarone® for the treatment and prevention of *plasmodium falciparum* malaria.

European Patent No. 123238 discloses 2-substituted-3-hydroxy-1,4-naphthoquinones, including atovaquone, which are said to be active against the human malaria parasite *Plasmodium falciparum* and also against *Eimeria* species such as *E. tenella* and *E. acervulina*, which are causative organisms of coccidiosis.

U.S. Pat. No. 5,053,432 and European Patent No. 123238 describe a process for preparing atovaquone (Scheme 1). The process as described in this patent proceeds by the reaction of 2-chloro-1,4-naphthoquinone and 4-(4-chlorophenyl)cyclohexane-1-carboxylic acid in the presence of silver nitrate and ammonium persulphate, followed by extraction with ether. This process gives an overall low yield due to the low yield produced in the key radical coupling stage.

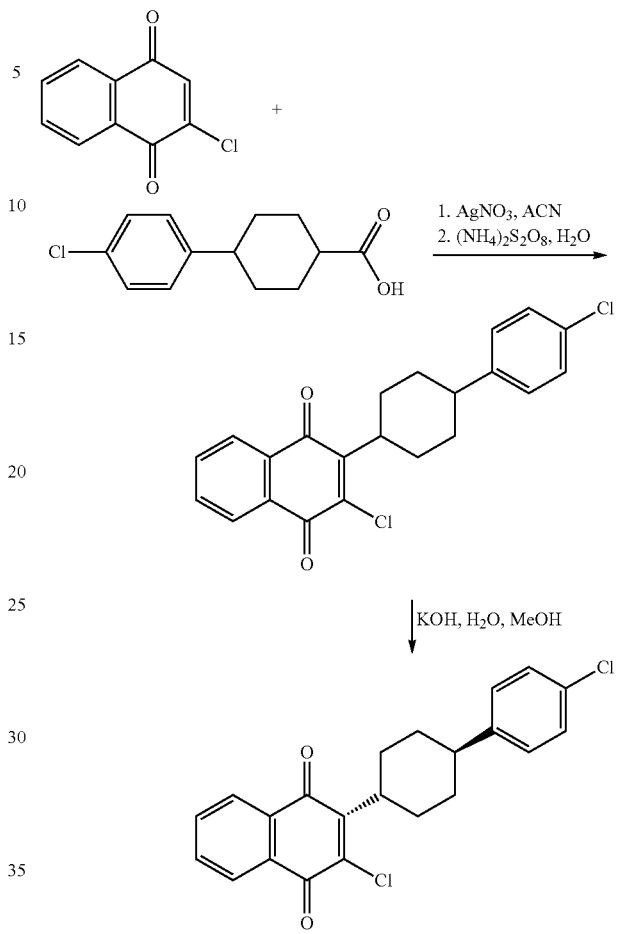

Scheme 1

A process for the preparation of atovaquone was also reported in Tetrahedron Letters, Vol. 39, 7629-7632 (1998), as shown in Scheme 2 below. This process prepares a mixture of cis and trans isomers of atovaquone by the reaction of an oxalate with 2-chloro-1,4-naphthquinone, in the presence of silver nitrate, ammonium persulphate and a phase transfer catalyst. The conversion to atovaquone was effected upon treatment with potassium hydroxide in methanol and recrystallisation from acetonitrile.

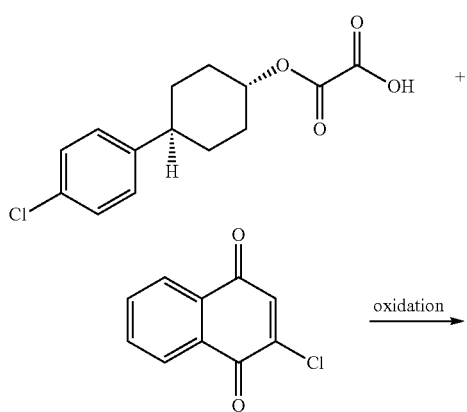

Scheme 2

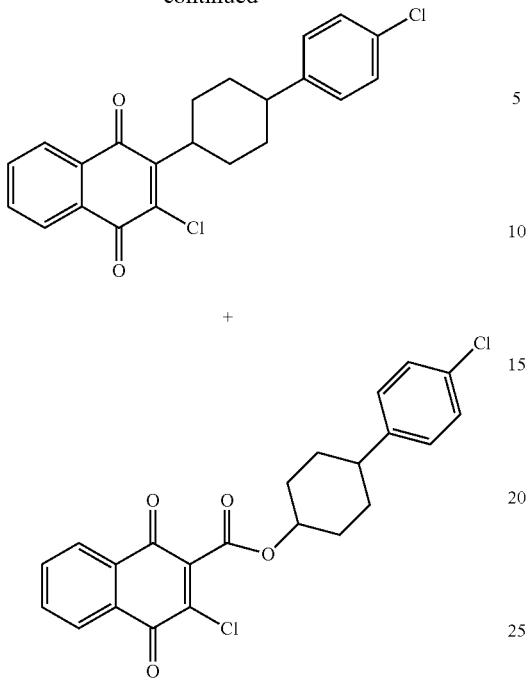

The disclosed process suffers from several drawbacks, as it requires purification by recrystallisation from acetonitrile. It also produces a low overall yield due to a low yield produced in the key radical coupling stage.

The object of this invention is therefore to develop an alternative process for the synthesis of atovaquone that does not suffer the draw backs of the prior art.

The processes herein described offer advantages over the prior art in that simpler reaction steps are included which increases the overall yield of the end product atovaquone. The processes herein described also use low cost starting materials. The processes herein described also do not include the use of silver nitrate (a heavy metal) which is expensive and may contaminate the final product with silver. Furthermore, the amount of silver in pharmaceuticals is tightly controlled by health authorities.

The process of the present invention avoids the use of highly undesirable agents such as acetonitrile, minimising environmental impact.

There is an unmet need for an improved process which provides higher yields of atovaquone, using reagents which are inexpensive while avoiding the use of undesirable reagents. The present invention provides such a process.

SUMMARY OF THE INVENTION

The present invention provides a new process for the preparation of atovaquone, which process comprises reacting 1H-2-benzopyran-1,4(3H)-dione (compound of formula (III)) with 4-(4-chlorophenyl)cyclohexanecarbaldehyde (compound of formula (IV)) to produce the novel intermediate (3Z)-3-{[4-(4-chlorophenyl)cyclohexyl]methylidene}-1H-2-benzopyran-1,4(3H)-dione (compound of formula (II)) which then undergoes internal rearrangement to produce atovaquone (compound of formula (I)).

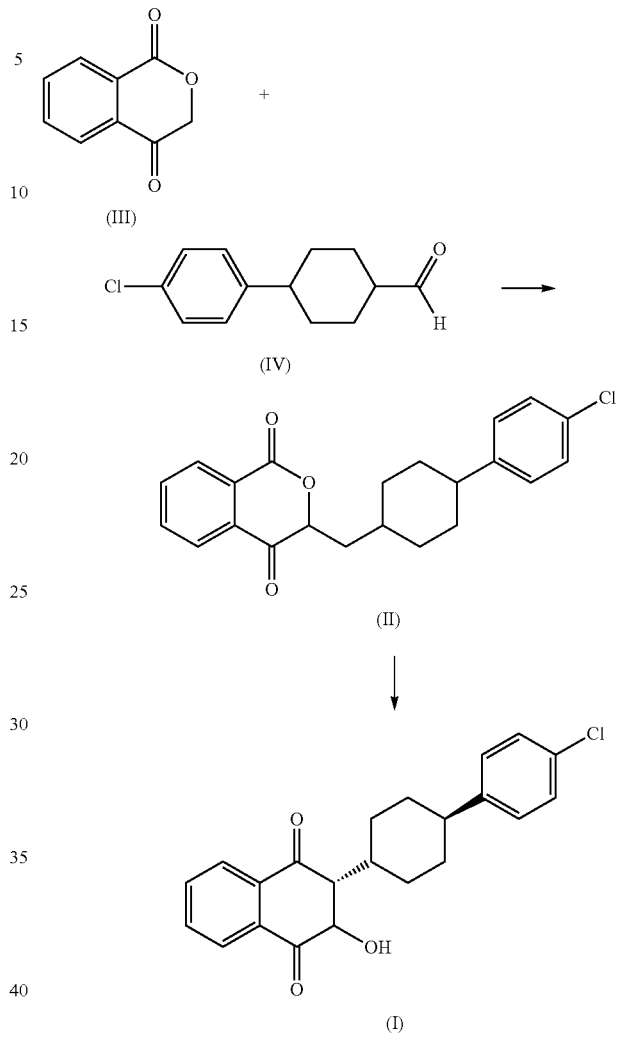

In another aspect, the invention also provides the novel intermediates (II), (V) and (VI) and uses thereof in the preparation of atovaquone.

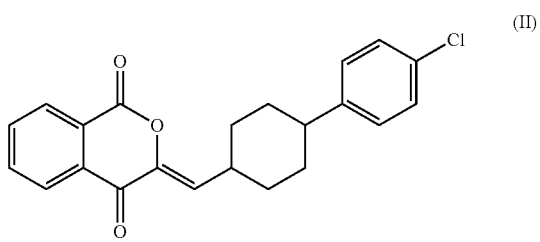

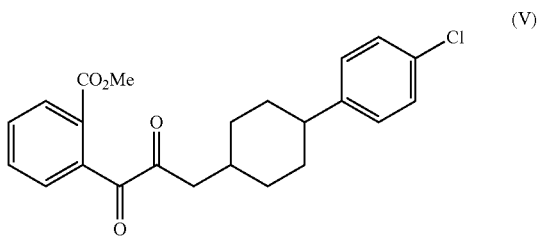

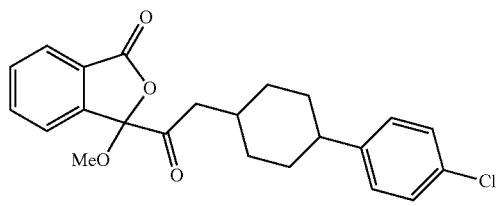

(VI)

DETAILED DESCRIPTION OF THE INVENTION

According to the present invention, there is provided a process for the preparation of atovaquone, said process comprising the steps of:

Scheme 4 a) Preparation of atovaquone (compound of formula (I)) by the conversion of (3Z)-3-{[4-(4-chlorophenyl)cyclohexyl]methylidene}-1H-2-benzopyran-1,4(3H)-dione (compound of formula (II));

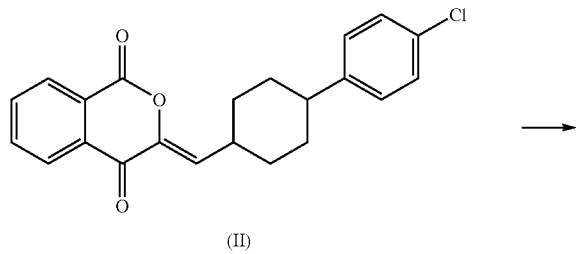

(II)

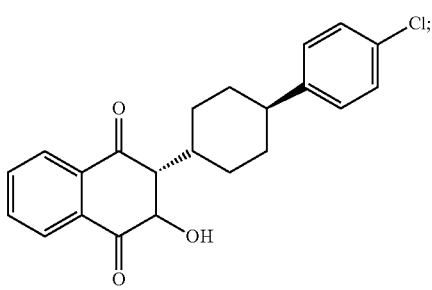

(I)

or b) Preparation of atovaquone (compound of formula (I)) by the conversion (3Z)-3-{[4-(4-chlorophenyl)cyclohexyl]methylidene}-1H-2-benzopyran-1,4(3H)-dione (compound of formula (II)) via methyl 2-{3-[4-(4-chlorophenyl)cyclohexyl]-2-oxopropanoyl}benzoate (compound of formula (V)) or 3-{[4-(4-chlorophenyl)cyclohexyl]acetyl}-3-(methyloxy)-2-benzofuran-1(3H)-one (compound of formula (VI));

Scheme 5

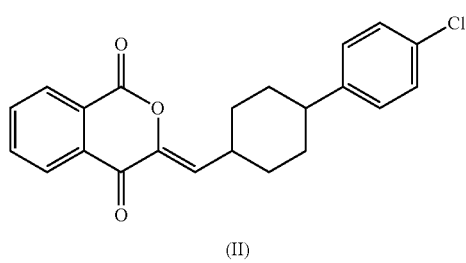

(II)

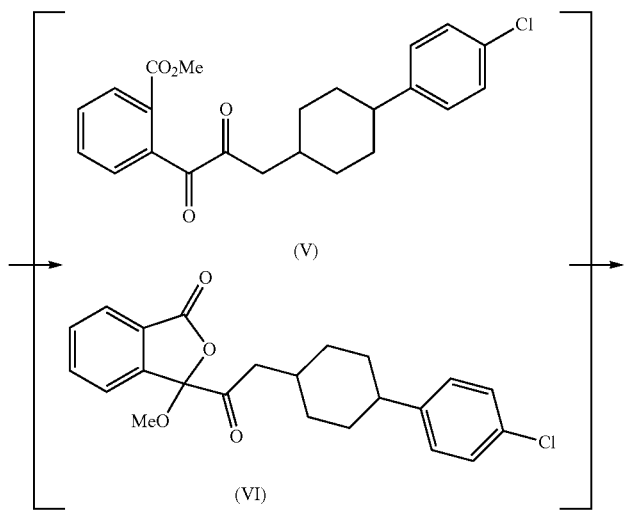

(V)

(VI)

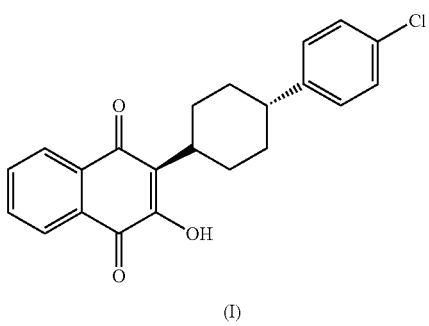

(I)

The present invention further provides a process for the preparation of intermediates:

c) Preparation of (3Z)-3-{[4-(4-chlorophenyl)cyclohexyl]methylidene}-1H-2-benzopyran-1,4(3H)-dione (compound of formula (II)) by the reaction of 1H-2-benzopyran-1,4(3H)-dione (compound of formula (III)) with 4-(4-chlorophenyl)cyclohexanecarbaldehyde (compound of formula (IV));

or e) Preparation of 4-(4-chlorophenyl)cyclohexanecarbaldehyde (compound of formula (IV)) by the reduction/Swern-oxidation of methyl 4-(4-chlorophenyl)cyclohexanecarboxylate (compound of formula (VII)) via (4-(4-chlorophenyl)cyclohexyl)methanol (compound of formula (VIII));

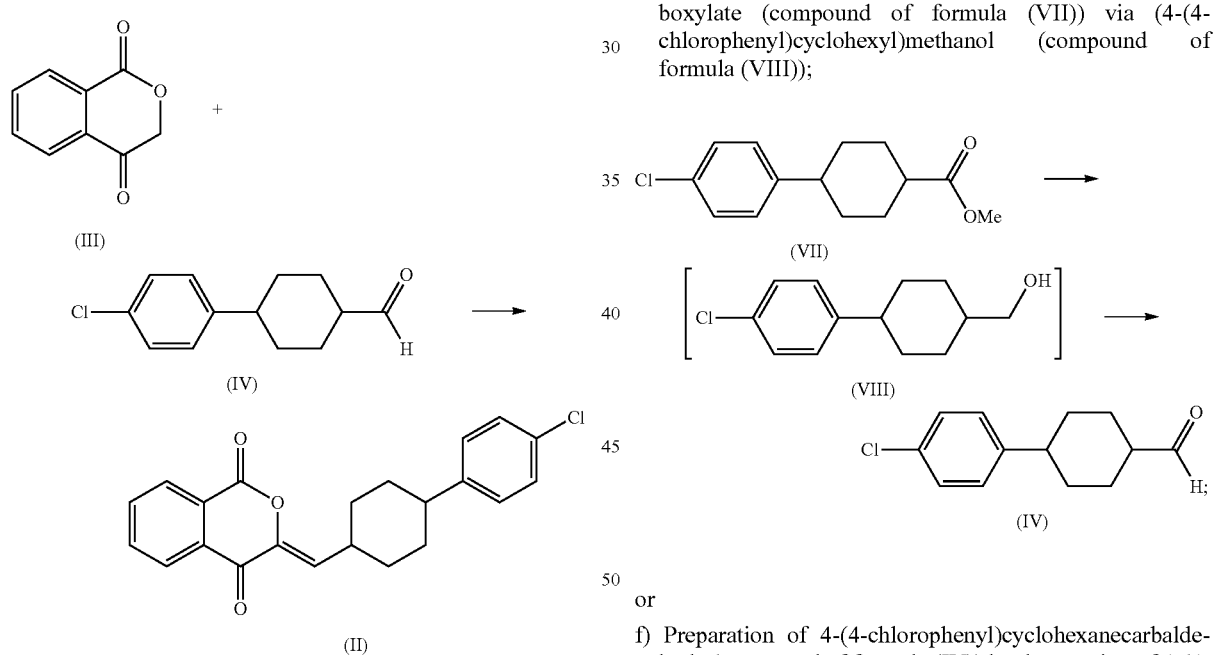

d) Preparation of 4-(4-chlorophenyl)cyclohexanecarbaldehyde (compound of formula (IV)) by the DIBAL reduction of methyl 4-(4-chlorophenyl)cyclohexanecarboxylate (compound of formula (VII));

or f) Preparation of 4-(4-chlorophenyl)cyclohexanecarbaldehyde (compound of formula (IV)) by the reaction of 4-(4-chlorophenyl)cyclohexane carboxylic acid (compound of formula (IX)) with oxalyl chloride, followed by palladium catalysed hydrogenation of 4-(4-chlorophenyl)cyclohexane carbonyl chloride (compound of formula (X));

Scheme 7

-continued

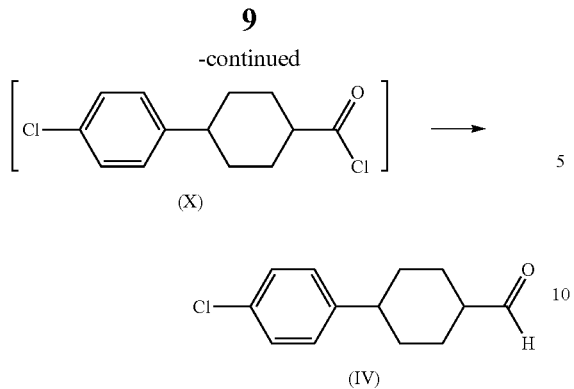

g) Preparation of 2-acetyl benzoic acid (compound of formula (XI)) by the reaction of phthalic anhydride (compound of formula (XII) with malonic acid (compound of formula (XIII));

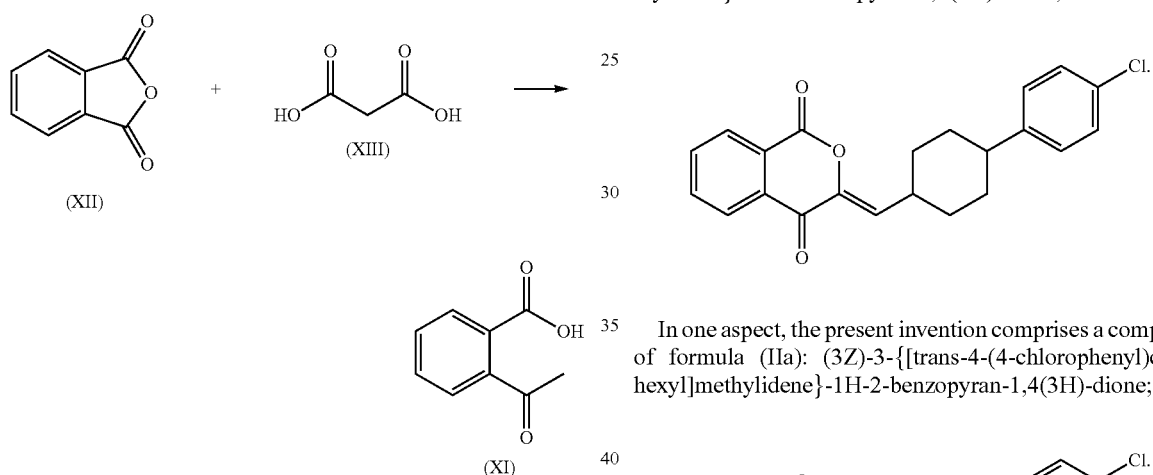

h) Preparation of 1H-2-benzopyran-1,4(3H)-dione (compound of formula (III)) by treating 2-acetyl benzoic acid (compound of formula (XI)) in the presence of a halogenating agent;

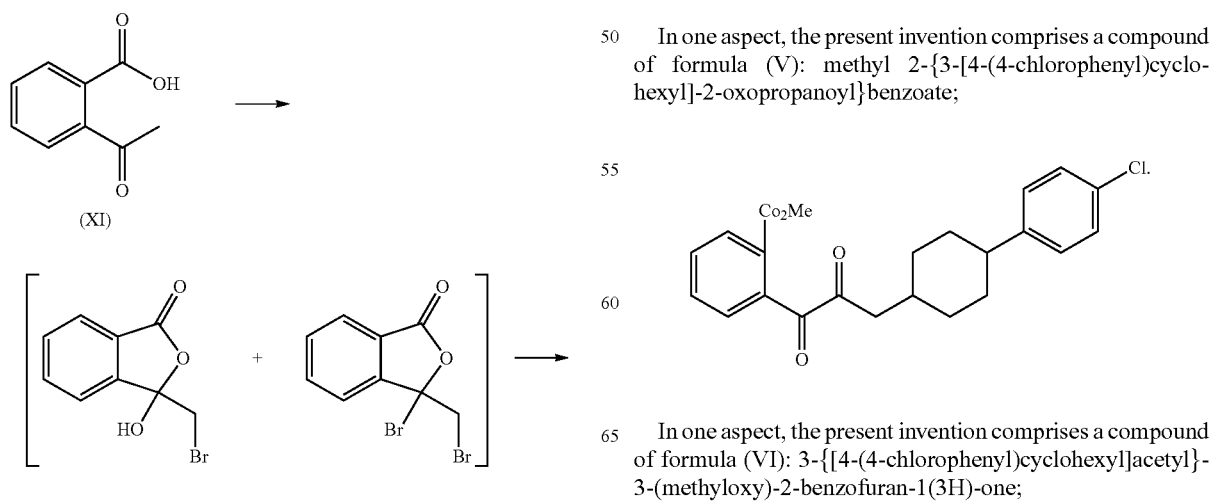

Each of the aspects of the invention are independent unless stated otherwise. Nevertheless the skilled person will understand that all the permutations of the aspects herein described are within the scope of the invention. Thus it is to be understood that the present invention covers all combinations of suitable, convenient and exemplified aspects described herein.

In one aspect, the present invention comprises a compound of formula (II): (3Z)-3-{[4-(4-chlorophenyl)cyclohexyl]methylidene}-1H-2-benzopyran-1,4(3H)-dione;

In one aspect, the present invention comprises a compound of formula (IIa): (3Z)-3-{[trans-4-(4-chlorophenyl)cyclohexyl]methylidene}-1H-2-benzopyran-1,4(3H)-dione;

In one aspect, the present invention comprises a compound of formula (V): methyl 2-{3-[4-(4-chlorophenyl)cyclohexyl]-2-oxopropanoyl}benzoate;

In one aspect, the present invention comprises a compound of formula (VI): 3-{[4-(4-chlorophenyl)cyclohexyl]acetyl}-3-(methyloxy)-2-benzofuran-1(3H)-one;

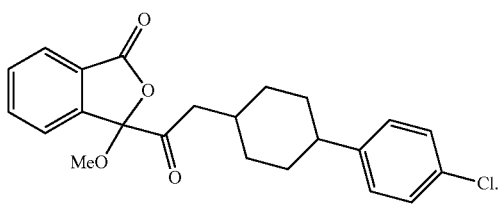

It will be appreciated that the compounds of formulae (II), (IV), (V), (VI), (VII), (VIII), (IX) and (X) may exist as the cis or trans isomer. Both cis and trans isomers and mixtures thereof in any ratio may be used in accordance with the present invention. In general when the compound is in the form of a mixture of isomers the trans isomer will be present in an amount of about 50% or will be the predominant isomer but the use of mixtures in which the cis isomer predominates is also included within the scope of the invention.

Scheme 4, Process a)

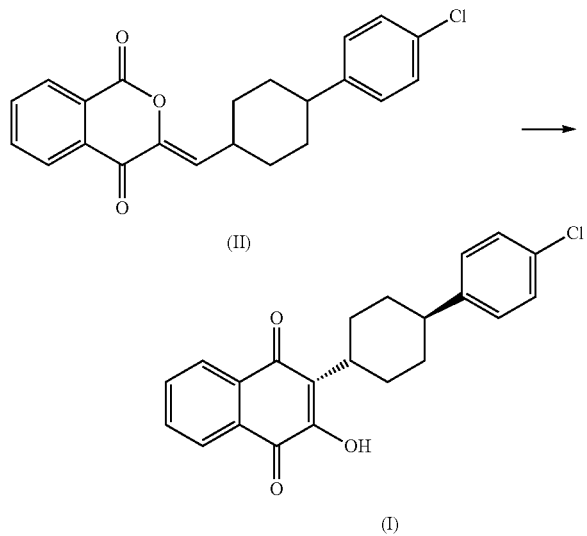

Compounds of formula (II) in either the cis, trans or mixture may be prepared by methods as described in Scheme 5 c).

In one aspect, process a) proceeds in the presence of a suitable nucleophile/base. In another aspect, the nucleophile/base is sodium methoxide (NaOMe). In another aspect, the nucleophile/base is sodium ethoxide (NaOEt).

In one aspect, process a) proceeds in the presence of a suitable nucleophile. In another aspect, the nucleophile is sodium methoxide (NaOMe). In another aspect, the nucleophile is sodium ethoxide (NaOEt).

In one aspect, process a) proceeds in the presence of a suitable base. In another aspect, the base is sodium methoxide (NaOMe). In another aspect, the base is sodium ethoxide (NaOEt).

In one aspect, process a) proceeds in the presence of a suitable solvent. In another aspect, the solvent is methanol. In another aspect, the solvent is toluene. In another aspect, the solvent is ethanol.

In one aspect, process a) proceeds in the presence of a suitable acid. In another aspect, the acid is acetic acid (AcOH). In another aspect, the acid is hydrochloric acid (HCl). In another aspect, the acid is phosphoric acid ($H_3PO_4$). In another aspect, the acid is sulphuric acid ($H_2SO_4$).

In one aspect, process a) proceeds at a temperature of 10° C. to 30° C. In another aspect, the temperature is 20° C. In one aspect, process a) proceeds at a temperature of 40° C. to 60° C. In another aspect, process a) proceeds at a temperature of 30° C. to 40° C. In another aspect, the temperature is 50° C.

Scheme 4, Process b)

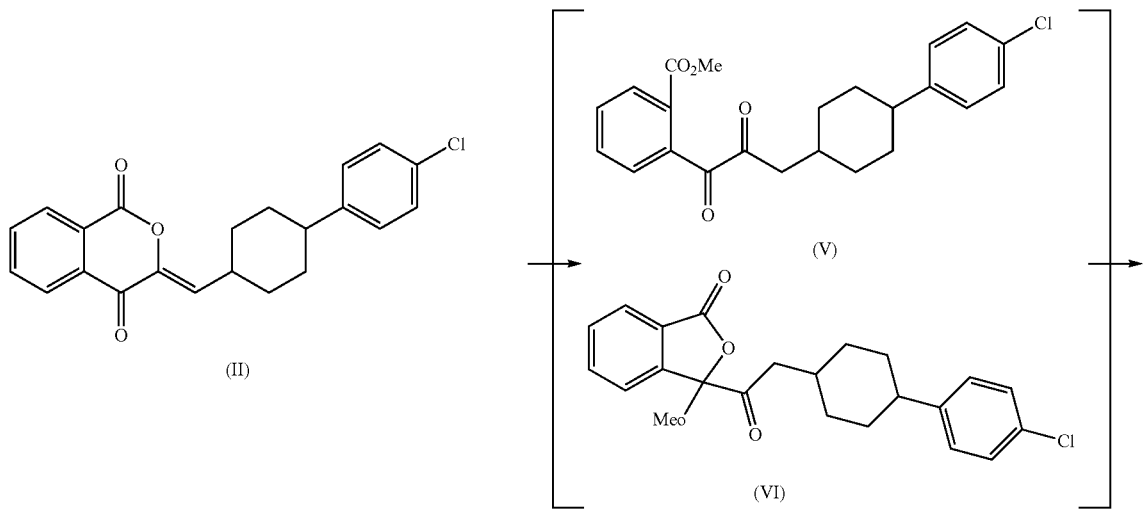

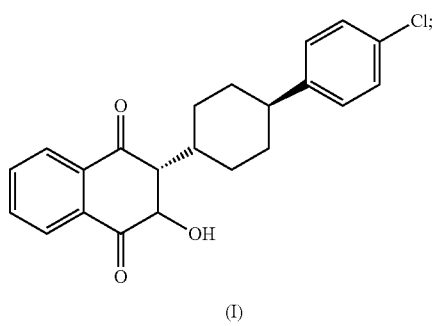

(I)

In one aspect, process b) proceeds in the presence of a suitable nucleophile/base. In another aspect, the nucleophile/base is DMAP (dimethylaminopyridine). In another aspect, the nucleophile/base is sodium methoxide.

In one aspect, process b) proceeds in the presence of a suitable nucleophile. In another aspect, the nucleophile is DMAP (dimethylaminopyridine). In another aspect, the nucleophile is sodium methoxide.

In one aspect, process b) proceeds in the presence of a suitable base. In another aspect, the base is DMAP (dimethylaminopyridine). In another aspect, the base is sodium methoxide.

In one aspect, process b) proceeds in the presence of a suitable solvent. In another aspect, the solvent is methanol. In another aspect, the solvent is toluene.

In one aspect, process b) proceeds in the presence of a suitable acid. In another aspect, the acid is phosphoric acid. In another aspect, the acid is acetic acid (AcOH). In another aspect, the acid is hydrochloric acid (HCl).

In one aspect, process b) proceeds at a temperature of 20° C. to 30° C. In another aspect, the temperature is room temperature.

Compounds of formula (III) may be prepared by methods as described in Scheme 7, process h).

Compounds of formula (IV) in either the cis, trans or mixture may be prepared by methods as described in Scheme 6, process d, e) or f).

In one aspect, process c) proceeds in the presence of a suitable catalyst. In another aspect, the catalyst is isobutylamine. In another aspect, the catalyst is morpholine. In another aspect, the catalyst is ammonium acetate.

In one aspect, process c) proceeds in the presence of a suitable base. In another aspect, the base is isobutylamine. In another aspect, the base is morpholine. In another aspect, the base is ammonium acetate.

In one aspect, process c) proceeds in the presence of a suitable solvent. In another aspect, the solvent is ethyl acetate (EtOAc). In another aspect, the solvent is acetic acid (AcOH). In another aspect, the solvent is isopropyl acetate.

In one aspect, process c) proceeds in the presence of a suitable acid. In another aspect, the acid is acetic acid (AcOH).

In one aspect, process c) proceeds at a temperature of 20° C. to 60° C. In another aspect, the temperature is 40° C.

Scheme 5, Process c)

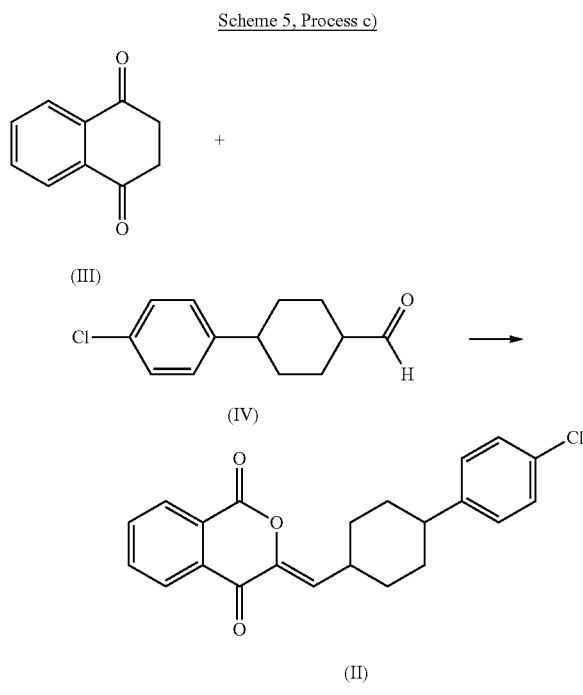

(II)

Scheme 6, Process d)

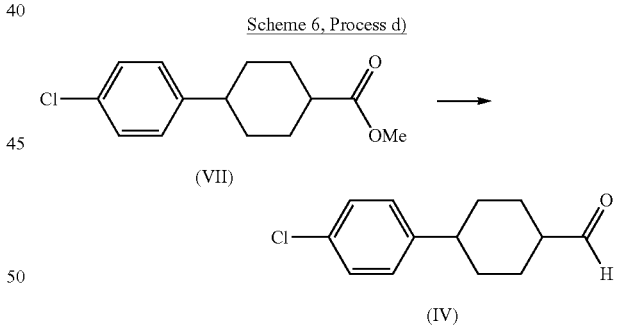

(IV)

Compounds of formula (VII) in either the cis, trans or mixture are commercially available or may be prepared by methods known to those skilled in the art.

In one aspect, process d) proceeds in the presence of a suitable reducing agent. In another aspect, the reducing agent is diisobutylaluminium hydride (DIBAL).

In one aspect, process d) proceeds in the presence of a suitable solvent. In another aspect, the solvent is dichloromethane (DCM). In another aspect, the solvent is toluene. In another aspect, the solvent is tetrahydrofuran (THF).

In one aspect, process d) proceeds in the presence of a suitable acid. In another aspect, the acid is hydrochloric acid. In another aspect, the acid is sulphuric acid. In another aspect, the acid is phosphoric acid.

In one aspect, process d) proceeds at a temperature of (−80° C.) to (−70° C.). In another aspect, the temperature is −78° C. In another aspect, process c) proceeds at a temperature of 0° C. to 20° C. In another aspect, the temperature is 10° C.

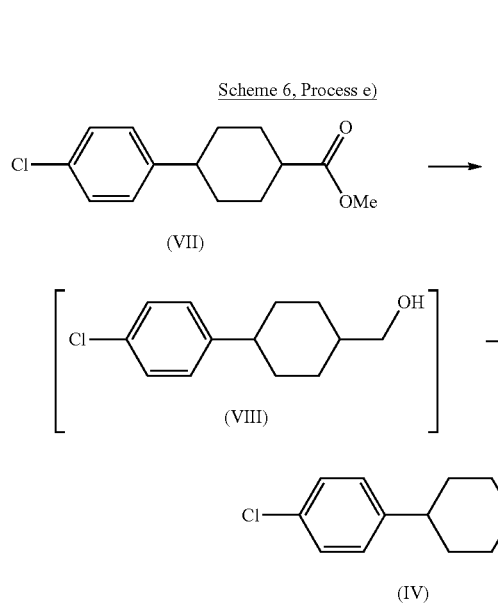

In one aspect, process e) proceeds in the presence of a suitable solvent. In another aspect, the solvent is tetrahydrofuran (THF). In another aspect, the solvent is ethyl acetate. In another aspect, the solvent is dimethyl sulfoxide (DMSO).

In one aspect, process e) proceeds in the presence of a suitable acid. In another aspect, the acid is hydrochloric acid. In another aspect, the acid is sulphuric acid. In another aspect, the acid is phosphoric acid.

In one aspect, process e) proceeds in the presence of a suitable reducing agent. In another aspect, the reducing agent is lithium aluminium hydride (LiAlH$_4$).

In one aspect, process e) proceeds in the presence of a suitable base. In another aspect, the base is triethylamine.

In one aspect, process e) proceeds at a temperature of −10° C. to 30° C. In another aspect, the temperature is 10° C.

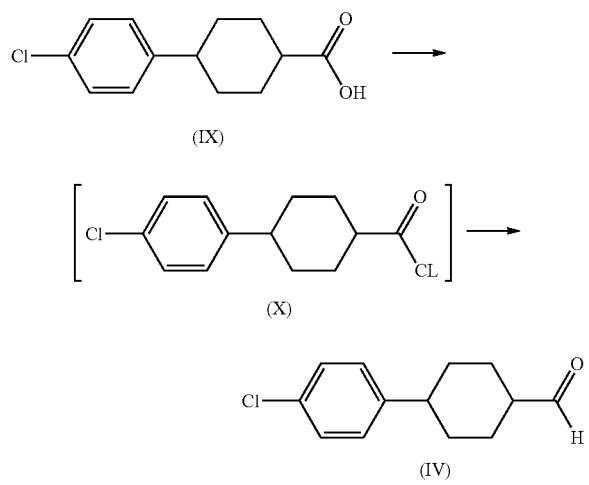

Compounds of formula (IX) in either the cis, trans or mixture are commercially available or may be prepared by methods known to those skilled in the art.

In one aspect, process f) proceeds in the presence of a suitable solvent. In another aspect, the solvent is ethyl acetate.

In one aspect, process f) proceeds in the presence of a suitable chlorinating agent. In another aspect, the chlorinating agent is oxalyl chloride. In another aspect, the chlorinating agent is thionyl chloride.

In one aspect, process f) proceeds in the presence of a suitable hydrogenating agent. In another aspect, the hydrogenating agent is hydrogen gas.

In one aspect, process f) proceeds in the presence of a suitable catalyst. In another aspect, the catalyst is Palladium (Pd) on carbon. In another aspect, the catalyst is dimethylformamide (DMF).

In one aspect, process f) proceeds at a temperature of 20° C. to 30° C. In another aspect, the temperature is room temperature.

In one aspect, process f) proceeds in the presence of a suitable base. In another aspect, the base is 2,6-lutidine. In another aspect, the base is quinaldine.

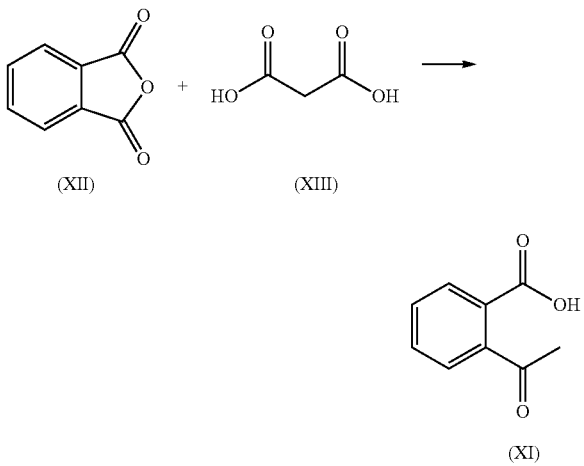

Compounds of formula (XII) and (XIII) are commercially available or may be prepared by methods known to those skilled in the art.

In one aspect, process g) proceeds in the presence of a suitable base. In another aspect, the base is triethylamine.

In one aspect, process g) proceeds in the presence of a suitable solvent. In another aspect, the solvent is triethylamine.

In one aspect, process g) proceeds at a temperature of 70 to 90° C. In another aspect, the temperature is 80° C.

In one aspect, process g) proceeds at a temperature of 20 to 30° C. In another aspect, the temperature is 25° C.

In one aspect, process g) proceeds in the presence of a suitable acid. In another aspect, the acid is hydrochloric acid. In another aspect, the acid is sulphuric acid. In another aspect, the acid is phosphoric acid.

Scheme 7, Process h)

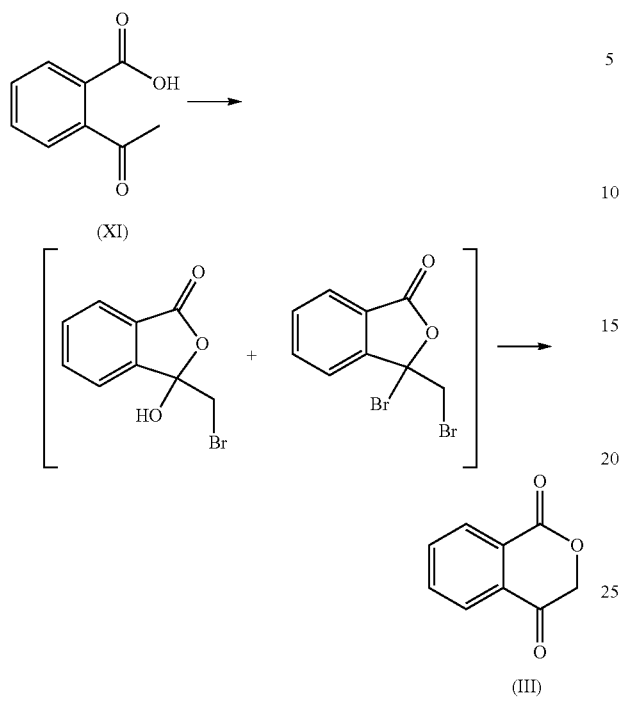

Compounds of formula (XI) are commercially available or may be prepared by methods known to those skilled in the art or as described in Scheme 7, process g).

In one aspect, process h) proceeds in the presence of a halogenating agent. In another aspect, the halogenating agent is a brominating agent. In another aspect, the halogenating agent is bromine ($Br_2$) or hydrobromic acid (HBr). In another aspect, the halogenating agent is hydrobromic acid (HBr). In another aspect, the halogenating agent is bromine ($Br_2$). In another aspect, the halogenating agent is a chlorinating agent. In another aspect, the halogenating agent is N-chlorosuccinimide (NCS).

In one aspect, process h) proceeds in the presence of a suitable solvent. In another aspect, the solvent is chlorobenzene. In another aspect, the solvent is propan-2-ol.

In another aspect, process h) proceeds in the presence of water.

In one aspect, process h) proceeds at a temperature of 30 to 40° C. In another aspect, the temperature is 30° C. In another aspect, the temperature is at reflux. In another aspect, the temperature is 60° C.

EXPERIMENTAL

Defintions h hours
CLR controlled laboratory reactor (jacketed vessel)
RM reaction mixture $^1$H NMR spectra were acquired on a Bruker Ultrashield DPX 400 (400 MHz) spectrometer. Samples were dissolved in DMSO-d6 or $CDCl_3$ and chemical shifts were reported in ppm relative to the solvent residual peak. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

$^{13}$C NMR spectra were acquired on a Bruker Ultrashield DPX 400 (400 MHz) spectrometer. Samples were dissolved in DMSO-d6 or $CDCl_3$ and chemical shifts were reported in ppm relative to the solvent residual peak. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Compounds are named using ACD/Name PRO6.02 chemical naming software (Advanced Chemistry Development Inc., Toronto, Ontario, M5H2L3, Canada).

Regardless of how the preparation of compounds are represented in the present specification no inference can be drawn that particular batches (or mixtures of two or more batches) of intermediates were used in the next stage of the preparation. The examples and intermediates are intended to illustrate the synthetic routes suitable for preparation of the same, to assist the skilled persons understanding of the present invention.

The invention is further illustrated by the following non-limiting examples.

Example 1

Preparation of 2-acetyl benzoic acid (Compound of formula (XI))

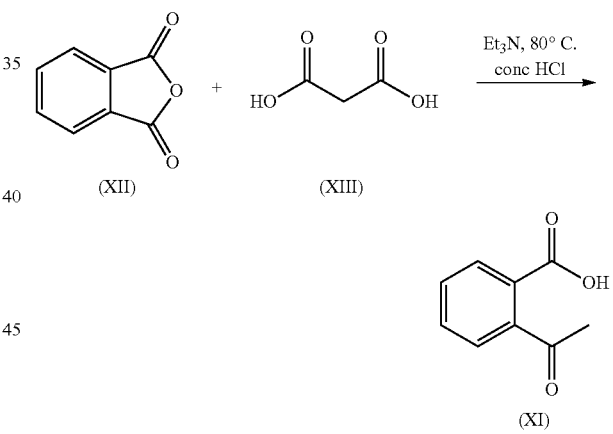

A stirred mixture of phthalic anhydride (compound of formula (XII)) (2.3 kg, 1 eq) (commercially available), malonic acid (compound of formula (XIII)) (389 g) (commercially available) and triethylamine (3.2 L) were heated to 80° C. Further portions of malonic acid (5×389 g; 1.94 kg total) were charged at 15 minute intervals and the reaction mixture maintained at 80° C. for 10 hrs. 4M hydrochloric acid (12.2 L) was charged and the reaction stirred for a further 30 minutes before being cooled to 25° C. and the resulting slurry filtered. The damp cake was washed with water (2×4 L) before being dried in vacuo at 50° C. to give the title compound (1.73 kg, 68%); $^1$H NMR (400 MHz, $CDCl_3$): δ 1.97 (3H, s, $CH_3$), 4.13 (1H, br s, OH) 7.52-7.63 (2H, m, CH Ar), 7.69-7.73 (1H, t, CH Ar), 7.84-7.86 (1H, d, CH Ar); $^{13}$C NMR (100 MHz, $CDCl_3$) δ 26.0, 106.6, 122.1, 125.4, 126.0, 130.5, 134.8, 149.8 and 169.3.

Example 2

Preparation of 1H-2-benzopyran-1,4(3H)-dione (Compound of formula (III))

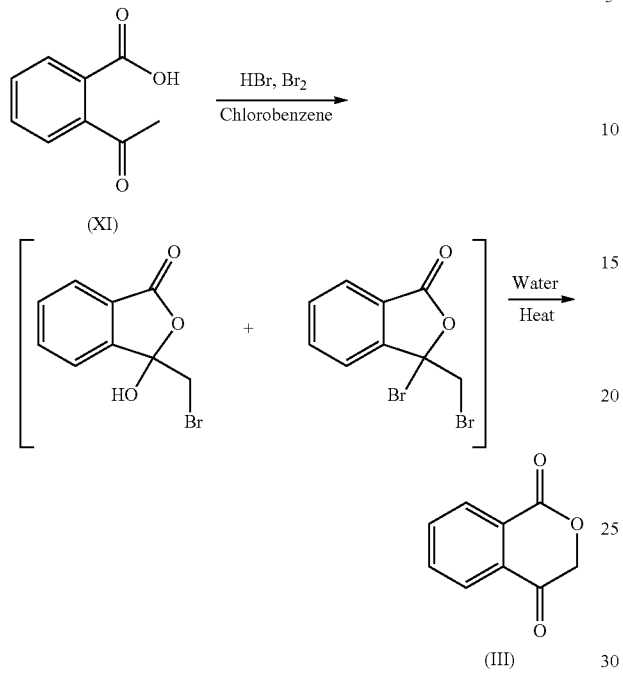

A stirred mixture of 2-acetylbenzoic acid (compound of formula (XI)) (1.00 Kg, 6.09 mol) and chlorobenzene (10.0 L) was treated with 5.5 molar hydrobromic acid in acetic acid (55 mL) and bromine (310 mL) then warmed to approximately 30° C. After 3 hours water (10.0 L) was added and the reaction heated to reflux. After 3 hours the reaction was cooled to 60° C. and the organic layer removed. The aqueous layer was extracted with chlorobenzene (2.0 L) and the combined organic layers concentrated under reduced pressure to approximately 3.0 L. Propan-2-ol (5.0 L) was charged and the slurry cooled to 0° C. before being filtered and washed with propan-2-ol (2.0 L). The resulting solid was dried in vacuo at 50° C. to give the title compound (736 g, 75%); $^1$H NMR (400 MHz, CDCl$_3$): δ 5.14 (2H, s, H-9), 7.82-7.91 (2H, m, H-2 and 3), 8.08-8.10 (1H, m, H-1), 8.28-8.30 (1H, m, H-4); $^{13}$C NMR (100 MHz, CDCl$_3$) δ 73.4, 125.6, 128.0, 130.9, 131.8, 134.7, 135.9, 161.4 and 189.5.

Example 3

Preparation of (3Z)-3-{[trans-4-(4-chlorophenyl)cyclohexyl]methylidene}-1H-2-benzopyran-1,4(3H)-dione (Compound of formula (IIa))

Stage 1: Preparation of trans-4-(4-chlorophenyl)cyclohexanecarbaldehyde (Compound of formula (IVa))

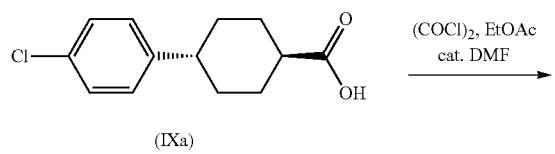

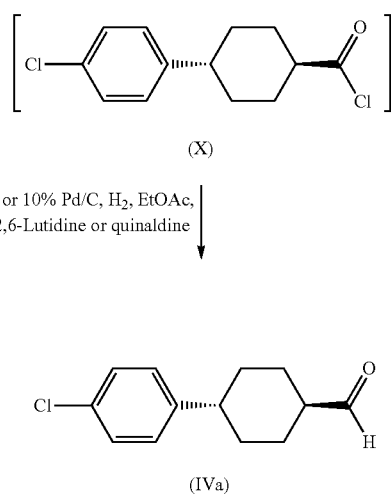

Example 3A

Stage 1

To a suspension of trans-4-(4-chlorophenyl)cyclohexanecarboxylic acid (compound of formula (IXa)) (4-CPCCA) (10.0 g, 41.9 mmol) in ethyl acetate (60 mL) was added catalytic DMF (20 µL). Oxalyl chloride (5.58 g, 44.0 mmol) was added dropwise over 30 mins and the mixture stirred at 55° C. until all solids had dissolved and complete reaction was determined by HPLC. The mixture was distilled to low volume (40 mL) and diluted with 2,6-lutidine (6.8 mL, 58.6 mmol). Dry activated carbon (0.5 g) was added and mixture stirred at room temperature for 15 mins. 10% w/w Pd on dry carbon powder (0.40 g) was added and the mixture stirred under hydrogen gas at 50 psi until complete reaction (18 hours). The resulting mixture containing the title compound was filtered and then used in the next step without analysis or purification.

Example 3B

Stage 1

A suspension of trans-4-(4-chlorophenyl)cyclohexanecarboxylic acid (compound of formula (IXa)) (4-CPCCA) (70.0 g, 293 mmol) in ethyl acetate (420 mL) with catalytic DMF (0.114 mL, 1.47 mmol) was heated to 55° C. and oxalyl chloride (27.0 mL, 308 mmol) was added, followed by a line wash of ethyl acetate (42 mL) This mixture was stirred at 55° C. until all solids had dissolved and the reaction was complete. The mixture was distilled down to low volume (210 mL), cooled to 20° C. and quinaldine (55.3 mL, 409 mmol) was added, followed by a line wash of ethyl acetate (42 mL). The mixture was transferred to a hydrogenation vessel containing 5% Pd/C (5.6 g, 0.08 wt), followed by a line wash of ethyl acetate (350 mL). The reaction mixture was stirred under hydrogen gas at 20° C. until complete reaction. The mixture was filtered to remove the catalyst, washing with ethyl acetate (154 mL) and was used in the next step without analysis or purification.

Stage 2: Preparation of (3Z)-3-{[trans-4-(4-chlorophenyl)cyclohexyl]methylidene}-1H-2-benzopyran-1,4(3H)-dione (Compound of formula (IIa))

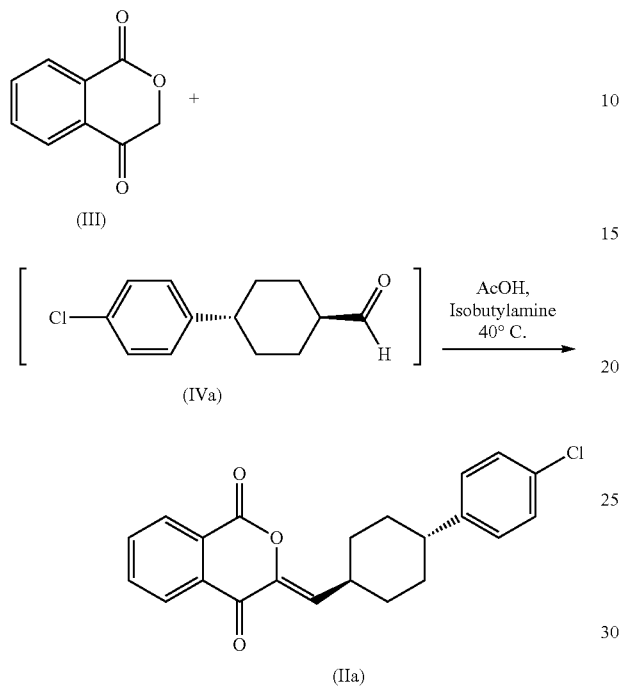

Example 3A

Stage 2

The filtrate obtained from stage 1 was treated with isobutylamine (1.25 mL, 12.6 mmol) and 1H-2-benzopyran-1,4(3H)-dione (compound of formula (III)) (6.52 g, 40.3 mmol). Acetic acid (70 mL) was added and the mixture warmed to 40° C. and stirred under $N_2$ (g) until complete reaction (3 hrs). The mixture was cooled to ambient and water (70 mL) added dropwise. The product was collected by filtration, washing with water (25 mL) and isopropanol (25 mL) before drying under vacuum at 50° C. to provide the title compound (11.7 g, 76%) as a colourless solid. $^1$H NMR (400 MHz, CDCl$_3$) $\delta_H$ 1.38-1.48 (2H, m, H-12$^a$ and H-16$^a$), 1.53-1.64 (2H, m, H-13$^a$ and H-15$^a$), 1.92-1.98 (4H, m, H-12$^b$, H-13$^b$ H-15$^b$ and H-16$^b$), 2.48-2.56 (1H, m, H-14), 2.88-3.00 (1H, m, H-11), 6.40 (1H, d, J=10.0, H-10), 7.14 (2H, m, H-18 and 22), 7.27 (2H, m, H-19 and 21), 7.86-7.91 (2H, m, H-2 and H-3), 8.25 (1H, m, H-1), 8.34 (1H, m, H-4); $^{13}$C NMR (100 MHz, CDCl$_3$) $\delta$ 31.3, 32.7, 33.8, 42.3, 126.1, 127.4, 128.1, 128.2, 128.3, 128.6, 129.0, 129.9, 135.1, 135.3, 145.5, 146.0, 176.4 and 194.1.

Example 3B

Stage 2

The mixture obtained from stage 1 was charged to a vessel at 20° C. followed by 1H-2-benzopyran-1,4(3H)-dione (compound of formula (III)) (45.5 g, 281 mmol washing with ethyl acetate (42 mL) followed by addition of acetic acid (210 mL) and isobutylamine (8.65 mL, 88 mmol) and a line wash of ethyl acetate (42 mL). The mixture was heated to 40° C. and stirred at this temperature until complete reaction and cooled to 20° C. The product was collected by filtration, washing with isopropanol (2×175 mL) before drying under vacuum at 70° C. Yield=77-78%. The material obtained was spectroscopically identical to that obtained by Example 3A.

Example 4

Preparation of atovaquone, 2-[trans-4-(4-chlorophenyl)cyclohexyl]-3-hydroxy-1,4-naphthalenedione (Compound of formula (I))

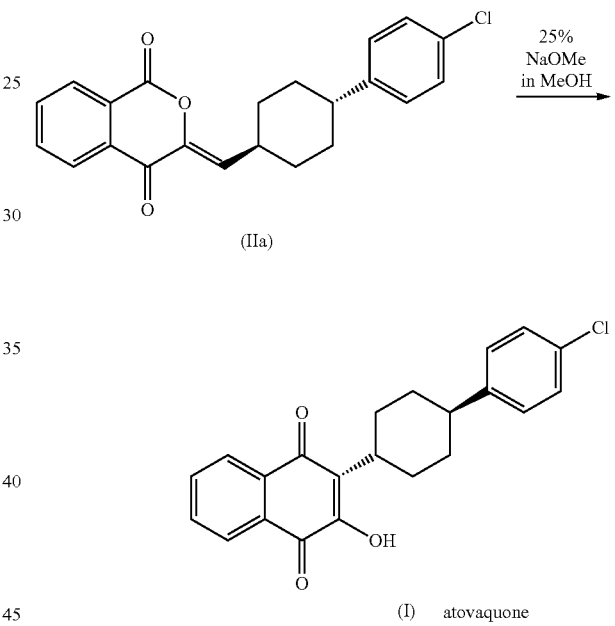

Example 4A

A 25 wt % solution of sodium methoxide in methanol (76.6 g, 0.354 mol) was added to a stirred suspension of (3Z)-3-{[trans-4-(4-chlorophenyl)cyclohexyl]methylidene}-1H-2-benzopyran-1,4(3H)-dione (compound of formula (IIa)) (100 g, 0.276 mol) in methanol (600 mL) at 20° C. The solids rapidly dissolved and the resulting dark red solution was stirred under $N_2$ (g) at 20° C. for 18 h or until conversion to atovaquone was complete. A solution of acetic acid (85.0 g, 1.42 mol) in water (21.3 g) was added to the stirred mixture with the precipitation of a bright yellow solid. The solid was collected by filtration, washed with methanol (250 ml) then dried to give the title compound as a bright yellow solid (91.12 g, 91%): $^1$H NMR (400 MHz, CDCl$_3$): $\delta$ 1.48-1.64

(2H, m, 2× cyclohexyl CH ax), 1.71-1.78 (2H, m, 2× cyclohexyl CH eq), 1.92-2.02 (2H, m, 2× cyclohexyl CH eq), 2.13-2.25 (2H, m, 2× cyclohexyl CH ax), 2.64 (1H, m, CHPhCl), 3.17 (1H, m, CHC=C(OH)), 7.18 (2H, d, CH Ar), 7.27 (2H, d, CH Ar), 7.48 (1H, s, OH), 7.68 (1H, m, CH Ar), 7.76 (1H, m, CH Ar), 8.08 (1H, d, CH Ar) and 8.14 (1H, d, CH Ar); $^{13}$C NMR (100 MHz, CDCl$_3$) δ 29.2, 34.4, 34.5, 43.3, 126.1, 127.0, 127.3, 128.2, 128.4, 129.2, 131.5, 132.9, 133.2, 135.0, 146.1, 153.0, 181.8.

Example 4B (3Z)-3-{[Trans-4-(4-chlorophenyl)cyclohexyl]methylidene}-1H-2-benzopyran-1,4(3H)-dione (compound of formula (IIa)) (15 g, 40.9 mmol) was slurried with methanol (90 mL, 6 vol) under N$_2$ and sodium methoxide (25%, 11.22 mL, 49.1 mmol) was added. The solution was allowed to stand for 29 hrs. A 250 ml CLR was charged with acetic acid (12.00 mL, 0.8 vol), water (3.00 mL, 0.2 vol) and methanol (45.0 mL, 3 vol). The RM was then added via pump to the vessel at ambient temperature. The slurry was stirred at ambient temperature for ca. 60 mins and the solid collected. The solid was washed with (a) water—methanol (1:1, 30 ml, 2 vol), (b) water—methanol (1:1, 30 ml, 2 vol) and (c) methanol (30 ml, 2 vol). The solid was dried (a) by suction and (b) in vacuo at ca. 50° C. to give the title compound (13.68 g, 91%). The material obtained was spectroscopically identical to that obtained by Example 4A.

Example 5

Preparation of (3Z)-3-{[trans-4-(4-chlorophenyl)cyclohexyl]methylidene}-1H-2-benzopyran-1,4(3H)-dione (Compound of formula (IIa))

Stage 1: Preparation of trans-4-(4-chlorophenyl)cyclohexanecarbaldehyde (Compound of formula (IVa))

To a stirred solution of methyl trans-4-(4-chlorophenyl)cyclohexanecarboxylate (compound of formula (VIIa)) (25.3 g, 100 mmol) in dichloromethane (250 mL) at −78° C. under argon was added a 1M solution of diisobutylaluminium hydride (DIBAL) in dichloromethane (110 mL, 110 mmol) and the mixture was stirred for 90 minutes. A further 5 mLs of DIBAL was then added. Methanol (125 mL) was added with stirring and the mixture allowed to warm to −10° C. 1M aqueous hydrochloric acid (250 mL, 250 mmol) was then added with stirring. The aqueous layer was extracted with dichloromethane (250 mL) and the combined organics washed twice with water (2×125 mL). The organics were concentrated under vacuum to a volume of 75 mL, the residue was diluted by the addition ethyl acetate (125 mL) and the mixture was then concentrated under vacuum to a volume of 75 mL. The resulting mixture containing the title compound was used in the next step without analysis or purification.

Stage 2: Preparation of (3Z)-3-{[trans-4-(4-chlorophenyl)cyclohexyl]methylidene}-1H-2-benzopyran-1,4(3H)-dione (Compound of formula (IIa))

To the resulting stirred mixture from stage 1, at ambient temperature under argon, was added acetic acid (125 mL), 1H-2-benzopyran-1,4(3H)-dione (compound of formula (III)) (16.2 g, 100 mmol) and ammonium acetate (7.7 g, 100 mmol). The reaction mixture was then heated to 70° C. and distilled for 2 hours. The resulting slurry was cooled to ambient temperature and water (75 mL) added. The slurry was stirred for 30 minutes at ambient temperature then filtered. The filter cake was washed with tert-butyl methyl ether (62.5 mL) and dried to give the title compound as a yellow solid (24.8 g). The material obtained was spectroscopically identical to that obtained in Stage 2, Example 3.

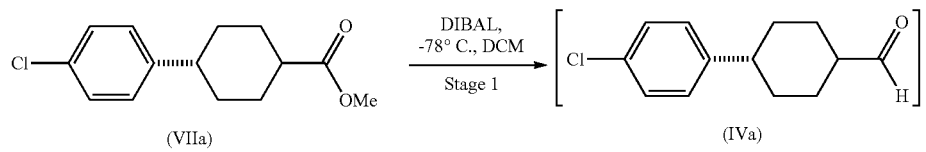

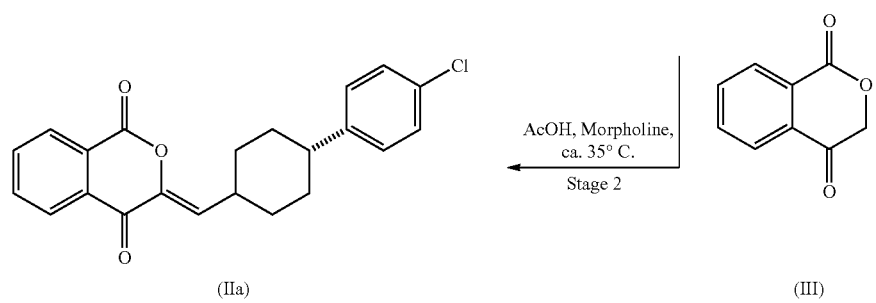

Example 6

Preparation of (3Z)-3-{[trans-4-(4-Chlorophenyl)cyclohexyl]methylidene}-1H-2-benzopyran-1,4(3H)-dione (Compound of formula (IIa))

Stage 1: Preparation of trans-4-(4-chlorophenyl)cyclohexanecarbaldehyde (Compound of formula (IVa))

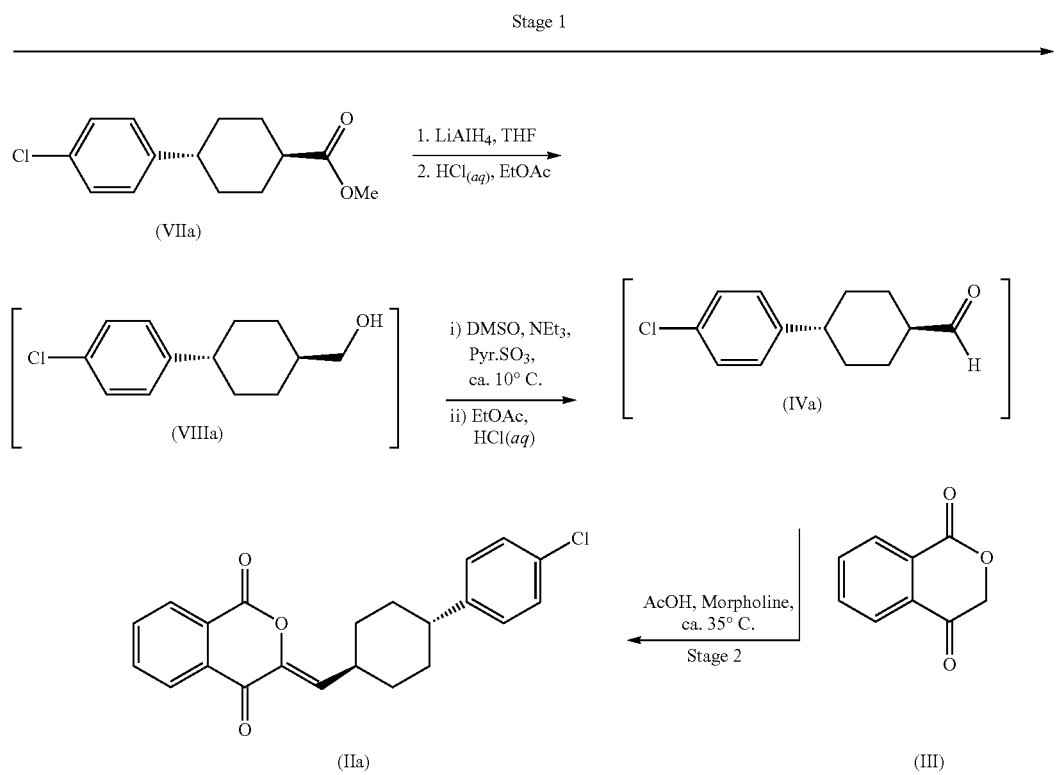

To a stirred solution of methyl trans-4-(4-chlorophenyl)cyclohexanecarboxylate (compound of formula (VIIa)) (50.5 g, 200 mmol) in tetrahydrofuran (400 mL) at 0° C. under argon was added a 1M solution of lithium aluminium hydride in tetrahydrofuran (100 mL, 100 mmol) and the reaction mixture stirred for 30 minutes. The reaction mixture was cooled to 0° C. and 1M aqueous hydrochloric acid (500 mL, 500 mmol) was added and the mixture stirred for 5 minutes. The aqueous was separated and extracted with ethyl acetate (250 mL) then the combined organics were washed twice with water (2×125 mL). The resulting organics were concentrated under vacuum to a volume of 150 mL. The residue was diluted with ethyl acetate (250 mL) and the mixture concentrated under vacuum to a volume of 150 mL. The residue was diluted with ethyl acetate (250 mL) and the mixture concentrated under vacuum to a volume of 150 mL. The residue was diluted with ethyl acetate (250 mL) and the mixture concentrated under vacuum to a volume of 150 mL. To the resulting stirred mixture, at ambient temperature under argon, was added dimethyl sulfoxide (100 mL) and triethylamine (112 mL, 804 mmol). The mixture was cooled to 0° C. then pyridine sulphur trioxide complex (64 g, 402 mmol) was added in 4 equal portions and the reaction mixture stirred between 0 and 20° C. for 2 hours. Ethyl acetate (400 mL) was added, the mixture cooled to 0° C. with stirring and then 1M aqueous hydrochloric acid (400 mL, 400 mmol) was added. The resulting mixture was stirred at ambient temperature for 5 minutes then the organic layer was separated, diluted by the addition of ethyl acetate (500 mL) and washed with water (250 mL). The resulting organics were concentrated under vacuum to a volume of 200 mL, the residue diluted by the addition of ethyl acetate (500 mL) and then concentrated to a volume of 200 mL. The resulting mixture containing the title compound was used in the next step without analysis or purification.

Stage 2: Preparation of (3Z)-3-{[trans-4-(4-chlorophenyl)cyclohexyl]methylidene}-1H-2-benzopyran-1,4(3H)-dione (Compound of formula (IIa))

To the resulting stirred mixture from stage 1, at ambient temperature under argon, was added acetic acid (250 mL), 1H-2-benzopyran-1,4(3H)-dione (compound of formula (III)) (32.4 g, 200 mmol) and morpholine (17.5 mL, 200 mmol). The reaction mixture was heated to 40° C. for 4 hours then allowed to cool to ambient temperature and stir overnight. Water (250 mL) was added and the slurry stirred for 15 minutes at ambient temperature then filtered. The filter cake was washed twice with tert-butyl methyl ether (2×125 mL) and dried to give the title compound as a yellow solid (62.4 g). The material obtained was spectroscopically identical to that obtained in Stage 2, Example 3.

Example 7a

Preparation of trans-4-(4-chlorophenyl)cyclohexanecarbaldehyde bisulfite complex (compound of formula (IVb))

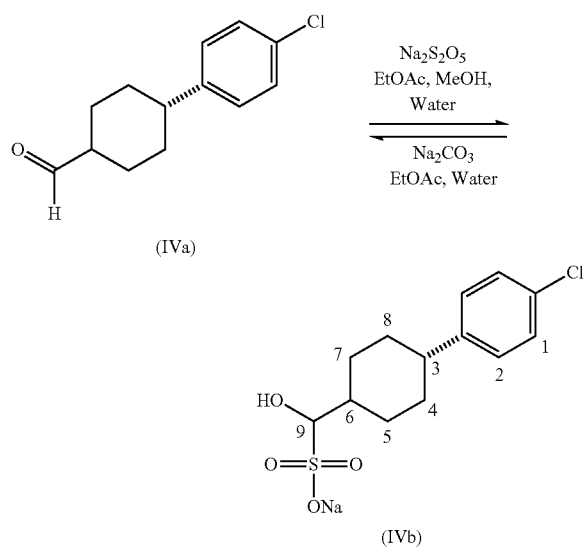

A stirred solution of trans-4-(4-chlorophenyl)cyclohexanecarbaldehyde (compound of formula (IVa) (approximately 9.33 g, 41.9 mmol, assuming quantitative conversion for preparation from trans-4-(4-chlorophenyl)cyclohexanecarboxylic acid) in EtOAc (100 mL) was charged with MeOH (40 mL), water (10 mL) and sodium metabisulfite (4.38 g, 0.55 eq). The resulting slurry was heated to 51° C., and stirred at this temperature for 45 min, the slurry was cooled to 20° C. over 1 hr then held for 30 min. The slurry was filtered and the cake washed with EtOAc (2×20 mL). The product was de-liquored then dried further in a 45° C. oven under reduced pressure to yield the title compound as a colourless solid (11.04 g, 81%). $^1$H NMR (400 MHz, d6-DMSO) δH 1.10-1.43 (4H, m, CH-alkyl), 1.70-1.80 (3H, m, CH-alkyl), 1.87-1.94 (1H, m, CH-alkyl), 2.12-2.21 (1H, m, CH-alkyl) 2.37-2.47 (1H, m, OH), 3.67 (1H, m, H-6), 4.79 (1H, m, H-9), 7.20-7.34 (4H, m, H-1 and H-2).

Example 7b

Preparation of trans-4-(4-chlorophenyl)cyclohexanecarbaldehyde (compound of formula (IVa))

A slurry of trans-4-(4-chlorophenyl)cyclohexanecarbaldehyde bisulfite complex (compound of formula (IVb)) (6.0 g), EtOAc (60 mL), water (30 mL) and sodium carbonate (2.14 g) was stirred at room temperature. The layers were allowed to settle overnight to separate. The organics were washed with water (30 mL), dried over sodium sulphate and concentrated to yield a colourless solid (2.60 g). $^1$H NMR (400 MHz, CDCl$_3$): δH 1.37-1.53 (4H, m, H-6ax, 7ax, 9ax and 10ax), 2.00-2.02 (2H, m, H-7 eq and 9 eq), 2.11-2.14 (2H, m, H-6 eq and 10 eq), 2.25-2.33 (1H, m, H-8), 2.45-2.51 (1H, m, H-5), 7.11-7.15 (2H, m) and 7.25-7.28 (2H, m, H-1,2,3 and 4), 9.68 (1H, s, H-11); $^{13}$C NMR (100 MHz, CDCl$_3$) δ 26.2, 32.9, 43.2, 49.8, 128.1, 128.5, 131.8, 145.1 and 204.3.

Example 8

Preparation of methyl 2-{3-[4-(4-chlorophenyl)cyclohexyl]-2-oxopropanoyl}benzoate (compound of formula (V))

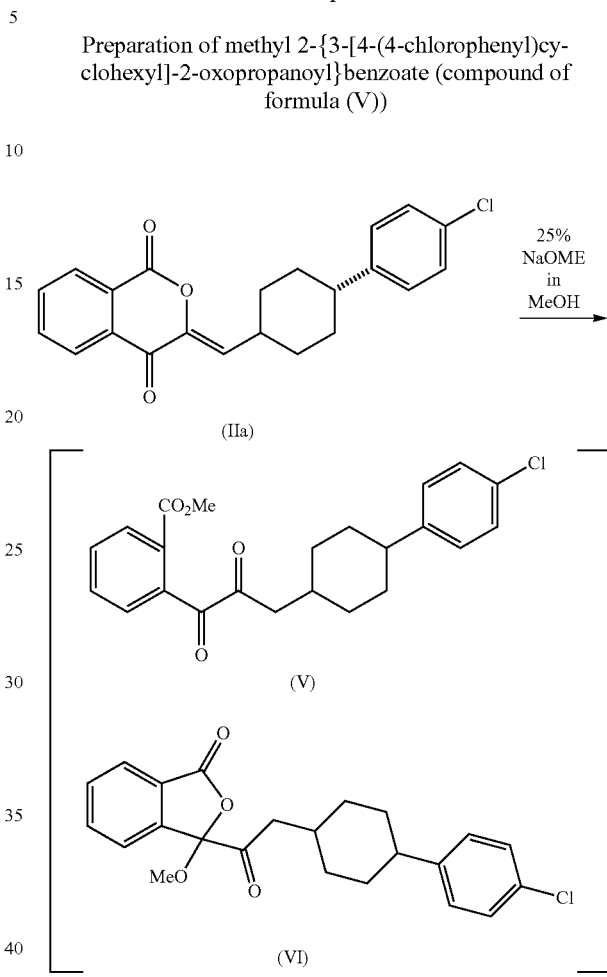

Stage 1

A suspension of (3Z)-3-{[trans-4-(4-chlorophenyl)cyclohexyl]methylidene}-1H-2-benzopyran-1,4(3H)-dione) (compound of formula (IIa)) (5.0 g, 13.63 mmol) and dimethylaminopyridine (67 mg, 0.55 mmol) in toluene (60 mL) and methanol (5 mL) was heated to 70° C. and stirred at this temperature for 7 h, cooled to ambient and stirred for 16 h. The solvent was removed under vacuum, diluted with tert-butylmethylether (20 mL) and this too was removed under vacuum to give the title compound as a bright yellow oil/gum (5.82 g, 107%).

Stage 2

Solid methyl 2-{3-[4-(4-chlorophenyl)cyclohexyl]-2-oxopropanoyl}benzoate (compound of formula (V)) was obtained by taking the yellow oil/gum (2.8 g) from stage 1 and adding methanol (20 mL) and triturating the mixture. The resulting off-white solid was collected by filtration under vacuum washed with methanol (5 mL) and dried (1.80 g, 64% recovery): $^1$H NMR (400 MHz, CDCl$_3$) δH 1.16-1.28 (2H, m, 2× cyclohexyl CH ax), 1.42-1.55 (2H, m, 2× cyclohexyl CH ax), 1.70-2.05 (5H, m, 4× cyclohexyl CH and CHCH$_2$C(O)), 2.44-2.54 (1H, m, CHPhCl), 2.95 (2H, d, CHCH₂C(O)), 3.87 (3H, s, CH₃), 7.12 (2H, d, CH Ar), 7.24 (2H, d, CH Ar), 7.48 (1H, d, CH Ar), 7.58 (1H, dd, CH Ar), 7.67 (1H, dd, CH Ar), 7.99 (1H, d, CH Ar); $^{13}$C NMR (100 MHz, CDCl₃) δ 32.7, 33.2, 34.0, 43.5, 43.6, 52.8, 128.2, 128.4, 129.0, 129.3, 129.4, 131.1, 131.4, 133.2, 138.9, 145.9, 167.1, 194.2 and 198.4.

Example 9

Preparation of atovaquone, 2-[trans-4-(4-chlorophenyl)cyclohexyl]-3-hydroxy-1,4-naphthalenedione (compound of formula (I))

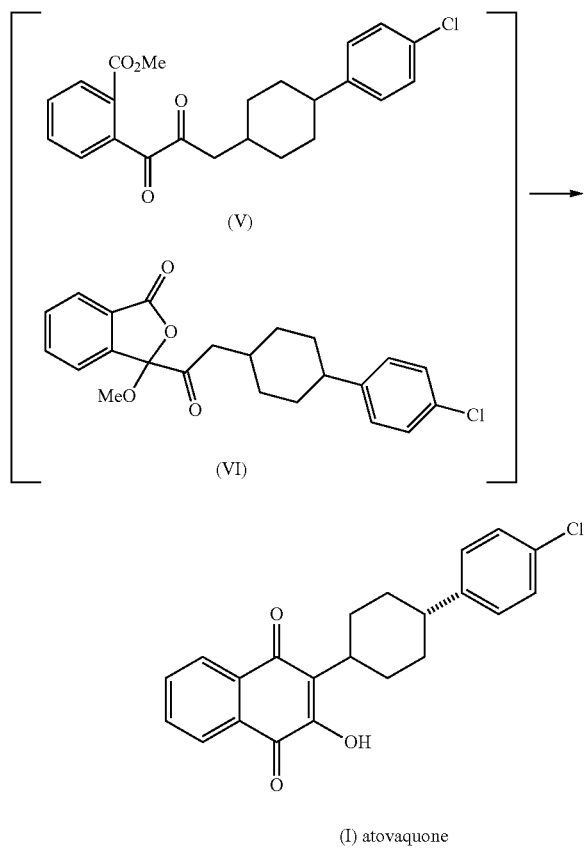

A quantity of the yellow oil/gum of methyl 2-{3-[4-(4-chlorophenyl)cyclohexyl]-2-oxopropanoyl}benzoate (compound of formula (V)) (3.0 g, 7.54 mmol) was diluted with methanol (18 mL) and stirred whereby a white solid precipitated. The slurry was treated with a 25% solution of sodium methoxide in methanol (2.02 g, 9.35 mmol) whereby solids began to dissolve and a red solution was formed. The solution was stirred at room temperature for 23 h, quenched by the dropwise addition of 5M phosphoric acid (1.8 mL, 9.0 mmol) and the resulting yellow slurry was stirred at room temperature for 24 h. The yellow suspension was filtered and the residue washed with methanol (4 mL+5 mL), hot water (2×9 mL) then dried to give the title compound as a bright yellow solid (2.30 g, 83%). The material obtained was spectroscopically identical to that obtained in Example 4.

Example 10

Preparation of 3-{[4-(4-(4-chlorophenyl)cyclohexyl] acetyl}-3-(methyloxy)-2-benzofuran-1(3H)-one (compound of formula (VI))

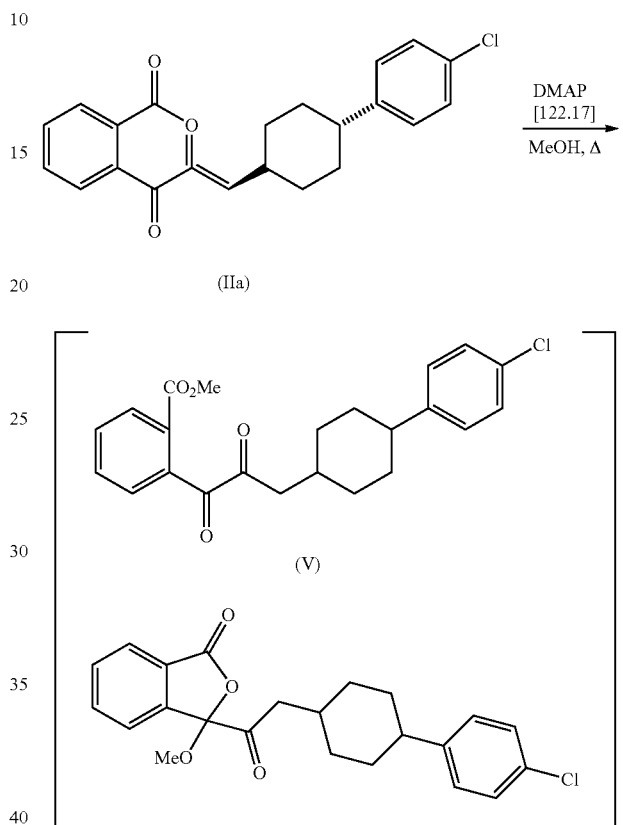

((3Z)-3-{[Trans-4-(4-Chlorophenyl)cyclohexyl]methylidene}-1H-2-benzopyran-1,4(3H)-dione) (compound of formula (IIa) (3.0 g, 8.18 mmol) and dimethylaminopyridine (0.12 g, 0.98 mmol) were suspended in methanol (60 mL), and the stirred mixture was heated at reflux for 25.5 h. The solution was allowed to cool to ambient, the solvent was removed under vacuum and the residue dissolved in tert-butylmethylether (20 mL) whereby white crystals started to crystallise. The mixture was allowed to stand at ambient overnight and the solid was collected by filtration under vacuum, washed with tert-butylmethylether (2×10 mL) and dried giving the title compound as white crystals (0.48 g, 14.7%): $^1$H NMR (400 MHz, CDCl₃) OH 0.98-1.15 (2H, m, 2× cyclohexyl CH ax), 1.36-1.51 (2H, m, 2× cyclohexyl CH eq), 1.70-1.98 (5H, m, 4× cyclohexyl CH and CHCH₂C(O)), 2.34-2.46 (1H, m, CHPhCl), 2.55 and 2.73 (2H, 2×dd, CHCH₂C(O)), 3.24 (3H, s, CH₃), 7.08 (2H, d, CH Ar), 7.24 (2H, d, CH Ar), 7.58 (1H, d, CH Ar), 7.64 (1H, dd, CH Ar), 7.75 (1H, dd, CH Ar), 7.94 (1H, d, CH Ar); $^{13}$C NMR (100 MHz, CDCl₃) δ 32.7, 32.9, 33.1, 33.8, 33.9, 43.5, 44.6, 52.1, 107.5, 124.2, 126.0, 127.6, 128.2, 128.4, 131.5, 131.6, 134.9, 142.72, 145.7, 167.8 and 201.1.

Example 11

Preparation of atovaquone, 2-[trans-4-(4-chlorophenyl)cyclohexyl]-3-hydroxy-1,4-naphthalenedione (compound of formula (I))

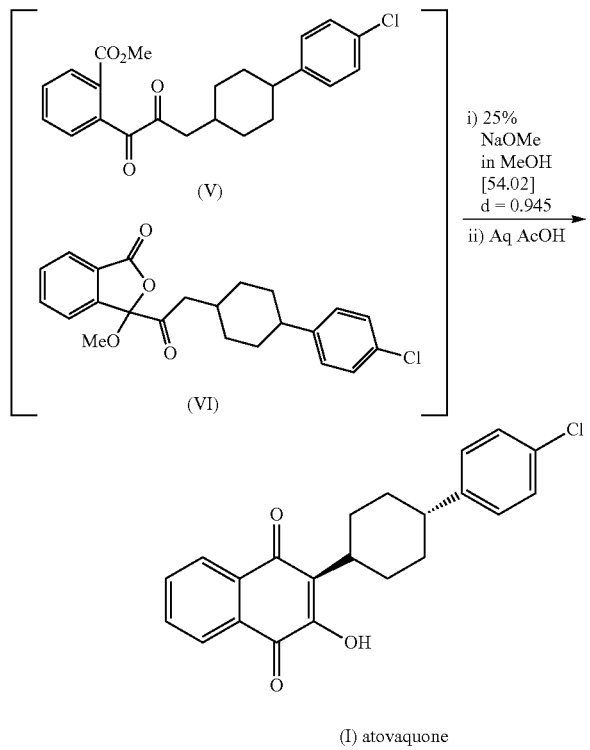

(I) atovaquone

A 25% solution of sodium methoxide in methanol (0.21 mL, 0.905 mmol) was added to a suspension of 3-{[4-(4-chlorophenyl)cyclohexyl]acetyl}-3-(methyloxy)-2-benzofuran-1(3H)-one (compound of formula (VI)) (0.30 g, 0.754 mmol) in methanol (2 mL) at room temperature. The solids gradually dissolved giving a red solution which was stirred at room temperature for 18 h, quenched by the dropwise addition of 5M phosphoric acid (0.2 mL, 1.0 mmol) and the resulting yellow slurry was stirred at room temperature for 24 h. The yellow suspension was filtered and the residue washed with methanol (2×1 mL), hot water (2×1 mL) then dried to give the title compound as a bright yellow solid (0.21 g, 76%). The material obtained was spectroscopically identical to that obtained in Example 4.

The invention claimed is:
1. A process for preparing atovaquone, the compound of formula (I)

comprising:
i. conversion of (3Z)-3-{[4-(4-chlorophenyl)cyclohexyl]methylidene}-1H-2-benzopyran-1,4(3H)-dione (compound of formula (II)) to atovaquone (compound of formula (I))

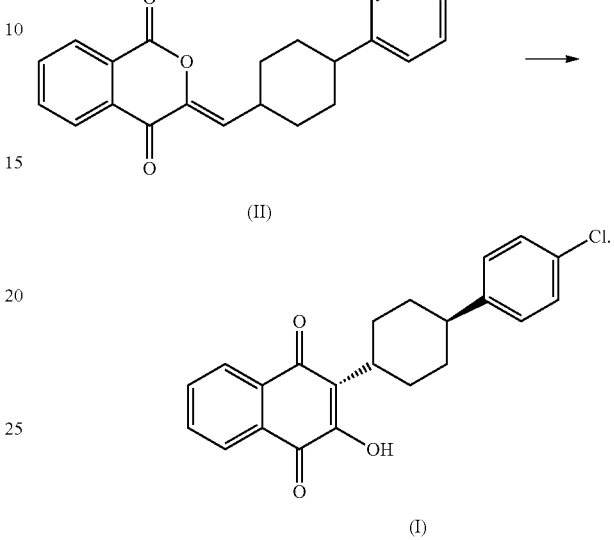

2. A process for preparing atovaquone, the compound of formula (I) according to claim 1 additionally comprising the step of:
ii. preparation of (3Z)-3-{[4-(4-chlorophenyl)cyclohexyl]methylidene}-1H-2-benzopyran-1,4(3H)-dione (compound of formula II) by reacting 1H-2-benzopyran-1,4(3H)-dione (compound of formula (III)) with 4-(4-chlorophenyl)cyclohexanecarbaldehyde (compound of formula (IV));

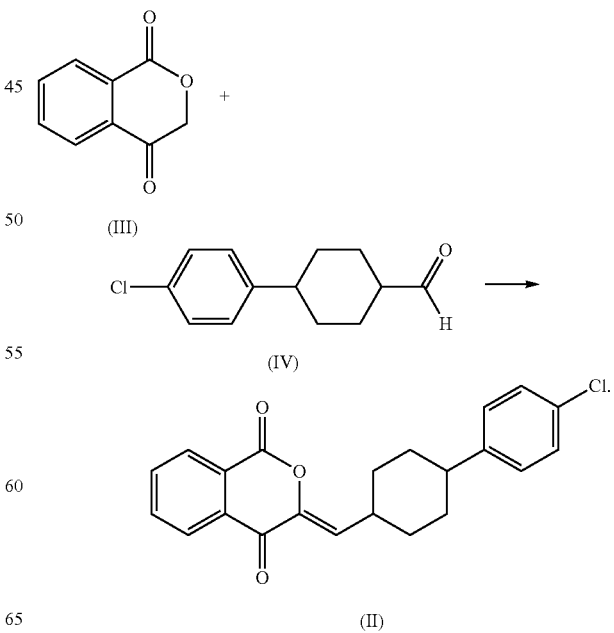

3. A process for preparing atovaquone, the compound of formula (I) according to claim 1 additionally comprising the step of:

iii. preparation of 4-(4-chlorophenyl)cyclohexanecarbaldehyde (compound of formula (IV)) by the reaction of 4-(4-chlorophenyl)cyclohexane carboxylic acid (compound of formula (IX)) with oxalyl chloride, followed by the hydrogenation of 4-(4-chlorophenyl)cyclohexane carbonyl chloride (compound of formula (X));

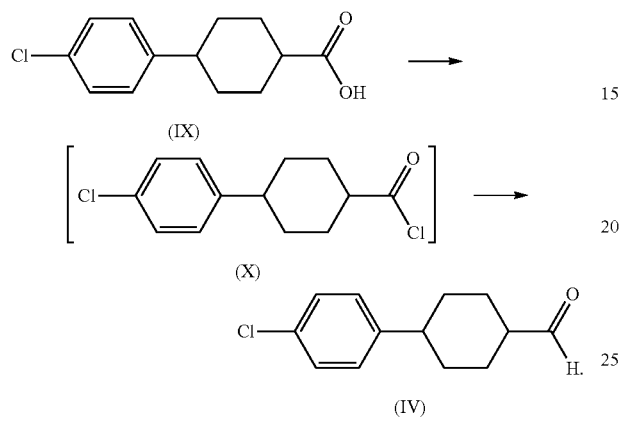

4. A process for preparing atovaquone, the compound of formula (I) according to 1 additionally comprising the step of:

iv. preparation of 1H-2-benzopyran-1,4(3H)-dione (compound of formula (III)) by treating 2-acetyl benzoic acid (compound of formula (XI)) with a suitable halogenating agent and cyclising the resulting intermediate(s);

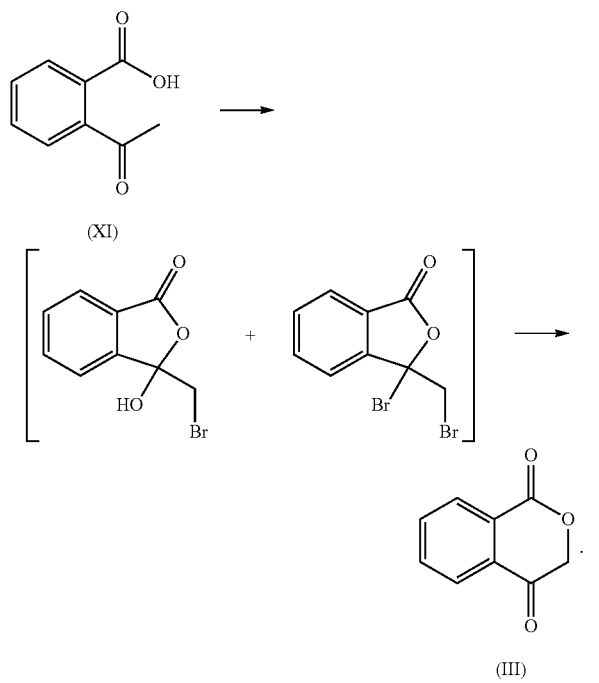

5. A process for preparing atovaquone, the compound of formula (I) according to claim 1 additionally comprising the step of:

v. preparation of 2-acetyl benzoic acid (compound of formula (XI)) by the reaction of phthalic anhydride (compound of formula (XI)) with maionic acid (compound of formula (XII));

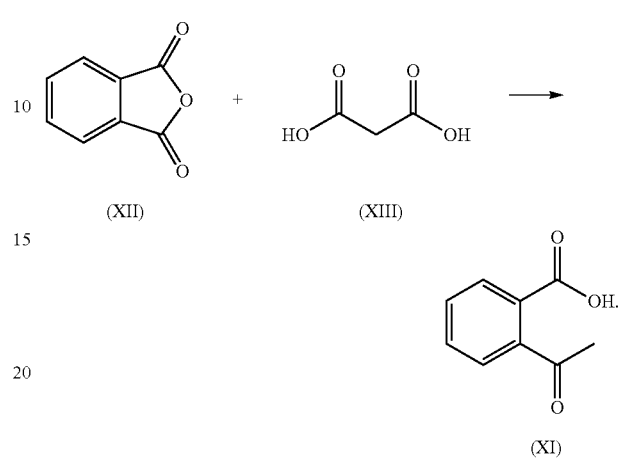

6. A process as claimed in claim 1 wherein the reaction proceeds in the presence of a nucleophile/base.

7. A process as claimed in claim 6 wherein the nucleophile/base is sodium methoxide (NaOMe).

8. A process as claimed in claim 2 wherein the reaction proceeds in the presence of a catalyst or a base.

9. A process as claimed in claim 8 wherein the catalyst or base is morpholine.

10. A process as claimed in claim 8 wherein the catalyst or base is isobutylamine.

11. A process as claimed in claim 3 wherein the hydrogenating agent is Pd/C and dry activated carbon.

12. A compound of the formula (II): (3Z)-3-{[4-(4-chlorophenyl)cyclohexyl]methylidene}-1H-2-benzopyran-1,4(3H)-dione

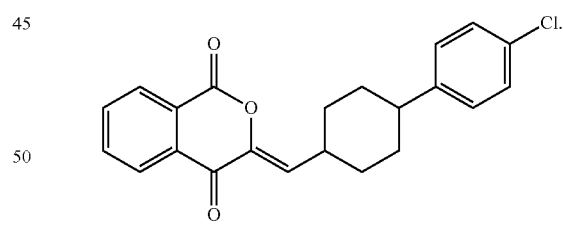

13. A compound of the formula (V): methyl 2-{3-[4-(4-chlorophenyl)cyclohexyl]-2-oxopropanoyl}benzoate

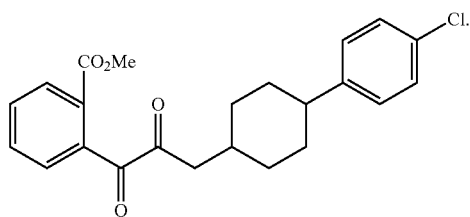

14. A compound of the formula (VI): 3-{[4-(4-chlorophenyl)cyclohexyl]acetyl}-3-(methyloxy)-2-benzofuran-1(3H)-one
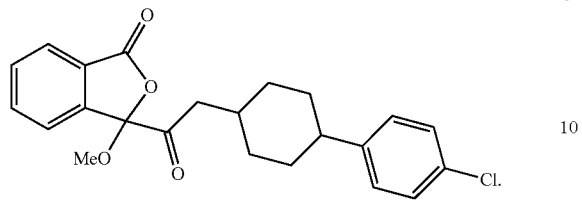
* * * * *